United States Patent [19]
McNamara

[11] Patent Number: 6,042,567
[45] Date of Patent: Mar. 28, 2000

[54] APPARATUS FOR THE INTRODUCTION OR REMOVAL OF FLUID BASED MATERIAL FROM A BLOOD VESSEL OF A PATIENT

[75] Inventor: Robert M. McNamara, Lafayette Hill, Pa.

[73] Assignee: Allegheny-Singer Research Institute, Pittsburgh, Pa.

[21] Appl. No.: 08/156,794

[22] Filed: Nov. 23, 1993

Related U.S. Application Data

[63] Continuation of application No. 07/810,675, Dec. 19, 1991, abandoned.

[51] Int. Cl.[7] ................................................ A61M 5/178
[52] U.S. Cl. ........................ 604/168; 604/169; 604/246; 604/256
[58] Field of Search .................... 604/164, 165, 604/167–170, 246, 248, 256, 283, 284, 900, 905

[56] References Cited

U.S. PATENT DOCUMENTS

| | | | |
|---|---|---|---|
| 3,774,604 | 11/1973 | Danielsson | 604/169 |
| 3,859,998 | 1/1975 | Thomas et al. | 604/168 |
| 4,073,297 | 2/1978 | Kopp . | |
| 4,079,738 | 3/1978 | Dunn . | |
| 4,230,128 | 10/1980 | Aramayo . | |
| 4,417,886 | 11/1983 | Frankhouser et al. | 604/170 |
| 4,966,586 | 10/1990 | Vaillancourt . | |
| 5,021,044 | 6/1991 | Sharkawy | 604/164 |
| 5,141,498 | 8/1992 | Christian | 604/167 |

FOREIGN PATENT DOCUMENTS

| | | | |
|---|---|---|---|
| 0183396 | 6/1986 | European Pat. Off. | 604/283 |
| 0370997 | 11/1989 | Germany . | |
| 9003822 | 4/1990 | WIPO | 604/289 |

*Primary Examiner*—Corrine McDermott
*Attorney, Agent, or Firm*—Ansel M. Schwartz

[57] ABSTRACT

An apparatus for the introduction or removal of fluid based material from a body of a patient by a clinician. The apparatus comprises a mechanism for connecting into a blood vessel of the patient's blood vessel to continuously introduce fluid based material into or remove the fluid based material from the patient's body. The connecting mechanism is fluidically sealed and self-sealing such that fluid based material cannot escape therefrom and contact the clinician at all times during installation and operation of the apparatus. The apparatus is also comprised of a device for controlling whether the fluid based material is introduced into or removed from the blood vessel while the connecting means is in contact with the blood vessel without the escape of the fluid based material therefrom. The controlling device is in fluidic communication with the connecting mechanism.

29 Claims, 4 Drawing Sheets

APPARATUS FOR THE INTRODUCTION OR REMOVAL OF FLUID BASED MATERIAL FROM A BLOOD VESSEL OF A PATIENT

This is a continuation of application(s) Ser. No. 07/810,675 filed on Dec. 19, 1991, now abandoned.

FIELD OF THE INVENTION

The present invention is related to the introduction or removal of fluid based material from a body of a patient. More specifically, the present invention is related to the introduction or removal of liquid based material from a blood vessel of a patient such that the material can escape therefrom and contact a clinician when the invention is in good condition and properly operated.

BACKGROUND OF THE INVENTION

Protection of a clinician, whether it be a physician or a non-physician, from the illness of a patient is an age old problem. The appearance of diseases such as Auto Immune Deficiency Syndrome (AIDS) has brought to the forefront of the medical community the need for effective protection of the clinician from the patient in all phases of the clinician's relationship with the patient. By doing so, the clinician is not only protected, but patients are also protected from risks of transfer of disease inadvertently through contact with clinicians who have been in contact with contaminated fluids from other patients.

An extremely common and important procedure that is performed by a clinician is the introduction or removal of fluid based material: be it, for instance, blood removed from the patient for testing, or, for instance, glucose introduced to the patient for nourishment. Each time such a procedure is performed, there exists the risk to the clinician that fluid based material from the patient will contact the clinician and transmit a harmful disease to the clinician or to others. Heretofore, there have been attempts to control or even solve this problem. The present invention serves to isolate the clinician from the fluid based material of the patient. The invention also protects patients from risks of transfer of disease from other patients inadvertently through contact with clinicians who have been in contact with contaminated fluids from other patients.

SUMMARY OF THE INVENTION

The present invention pertains to an apparatus for the introduction or removal of liquid based material from a blood vessel of a patient by a clinician. The apparatus comprises means for connecting into the blood vessel of the patient's body to continuously introduce liquid based material into or remove liquid based material from blood vessel. The connecting means is fluidically sealed and self-sealing such that the liquid based material is prevented from escaping from the apparatus and coming into contact with the clinician at all times during installation and operation of the apparatus. The apparatus is also comprised of means for controlling whether the fluid based material is introduced into or removed from the blood vessel while the connecting means is in contact with the blood vessel without the escape of liquid based material therefrom. The controlling means is in fluidic communication with the connecting means.

In a preferred embodiment, the connecting means includes a guide mechanism, such as a needle, which accesses the interior of the body. The connecting means can also include a catheter disposed about the guide mechanism.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figures 1, 3:
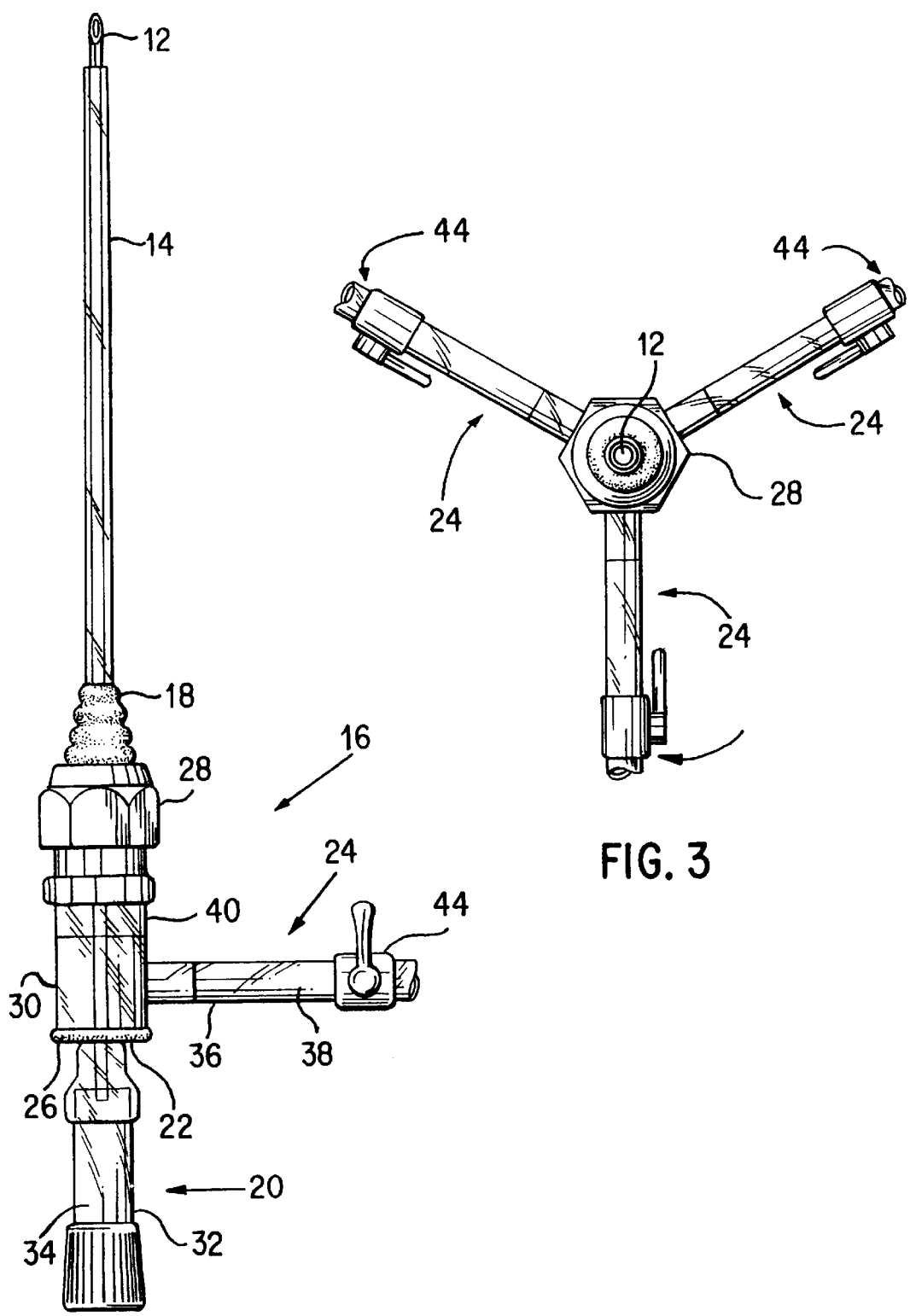
FIG. 1 is a schematic representation of a preferred embodiment of the apparatus of the present invention.
FIG. 3 is a schematic representation of an overhead cross-sectional view of an embodiment of the present invention having N side ports.

Referring now to the drawings wherein like reference numerals refer to similar or identical parts throughout the several views, and more specifically to FIG. 1 thereof, there is shown a schematic representation of an apparatus 10 for the introduction or removal of fluid and preferably liquid based material from a blood vessel of a patient by a clinician. The apparatus 10 comprises means for connecting into the interior of a blood vessel to continuously introduce fluid based material into or remove fluid based material from the blood vessel. The connecting means is fluidically sealed and self-sealing such that the fluid based material is prevented from escaping from the apparatus and coming into contact with the clinician at all times during installation and operation of the apparatus. The apparatus 10 is also comprised of means for controlling whether fluid based material is introduced into or removed from the blood vessel while the connecting means is in contact with the blood vessel without the escape of the same therefrom. The controlling means is in fluidic communication with the connecting means.

Figure 2:
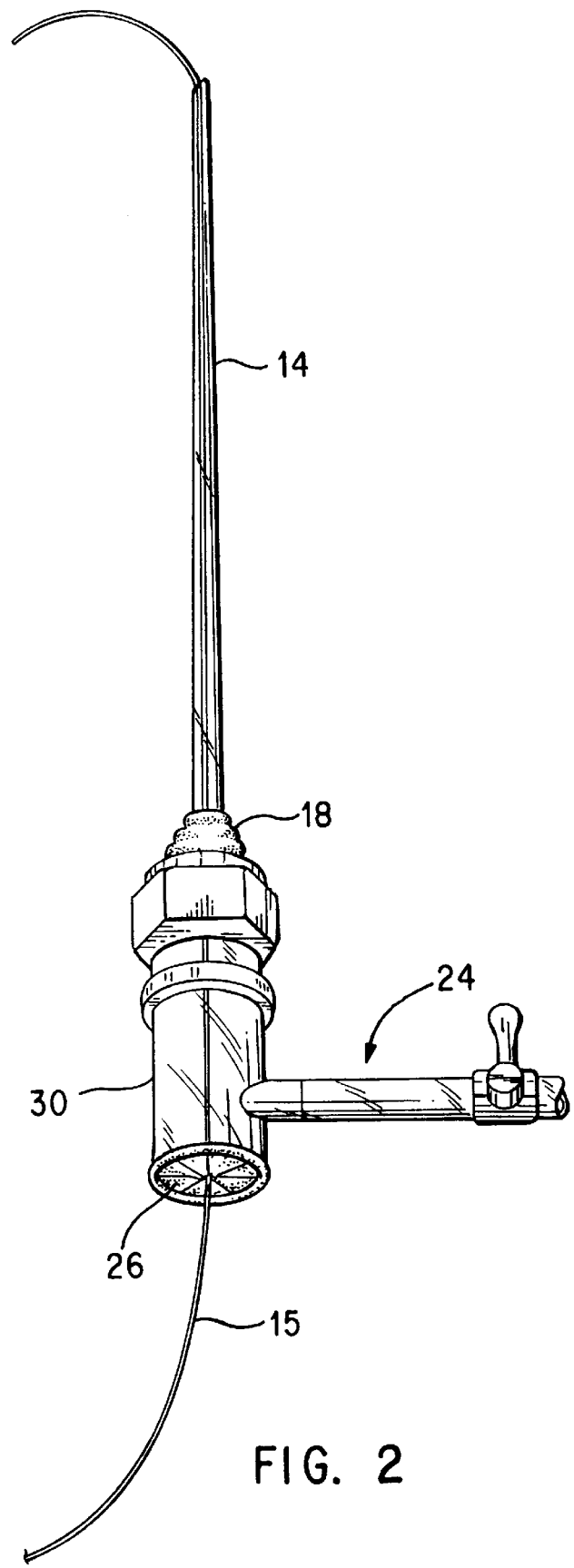
FIG. 2 is a schematic representation of an alternative embodiment of the apparatus of the present invention.

The connecting means preferably includes a guide mechanism which accesses the blood vessel. The connecting means also preferably includes a catheter 14 disposed about the guide mechanism. The guide mechanism is preferably a hollow needle 12, although, for instance, a guidewire 15 could be used, as shown in FIG. 2. The guidewire 15 would be placed into the interior of the patient with a separate needle which is then removed. The catheter 14 of the apparatus 10 is then advanced over the guidewire 15 into the blood vessel. Once the catheter is in place, the guidewire 15 is removed as described below. In the alternative, the hollow needle 12 can serve as both the guide mechanism and the means by which the blood vessel of the patient's body is reached so fluid is extracted from or introduced to the patient's body.

The connecting means can include a hollow central portion 16 having a first end 18 to which the catheter 14 is sealingly fixed such that movement of the central portion 16 and the catheter 14 occurs in unison. The connecting means can additionally include a flashback chamber 20 fluidically connected to the central portion 16 at a second end 22 thereof. The needle 12 preferably extends through the central portion 16 and into the flashback chamber 20 by way of the first end 18 and second end 22 of the central portion 16 such that fluid based material flowing into the needle 12 from the body fills the flashback chamber 20. The needle 12 is sealingly fixed to the flashback chamber 20 and sealingly but slidingly connected to the central portion 16 such that separation of the flashback chamber 20 from the central portion 16 results in separation of the needle 12 from the central portion 16 and the catheter 14 without the escape of any fluid based material from the central portion 16 or the flashback chamber 20. The controlling means is in fluidic connection with the central portion 16.

The central portion 16 can include N side ports 24, where N≧1, in fluidic connection with the controlling means through which fluidic connection to desired objects can be made as shown in FIG. 3. Preferably, the central portion 16 has one side port 24 as shown in FIG. 1. The central portion 16 preferably has at its second end 22 a self-sealing rubber diaphragm 26 through which the needle 12 sealingly but slidingly extends. Alternatively, if a guidewire 15 is used after the catheter 14 is advanced over it, the guidewire 15 extends out the second end 22 of the apparatus 10 through the diaphragm 26. Once the catheter 14 is in place, the guidewire 15 is then pulled out of the apparatus 10 via the second end 22. In general, any component that serves to seal the central portion 16 after removal of the catheter 14 or the guidewire 15, such as a twist closure, can also be used.

Preferably, the central portion 16 includes a catheter hub 28 having the first end 18, and a side port hub 30 having the second end 22 and from which the side port 24 extends. The side port hub 30 is sealingly and fixedly attached to the catheter hub 28.

The flashback chamber 20 preferably has a first transparent portion 32 through which the chamber interior 34 can be reviewed by the clinician. The side port 24 preferably has a second transparent portion 36 through which the side port interior 38 can be viewed by the clinician. The side port hub 28 can also have a third transparent portion 40 through which the side port hub's interior 42 can be viewed. It should be noted that the transparent portions can essentially be as large as desired. Preferably, the controlling means includes a valve such as a two-way stopcock 44 in fluidic connection with each side port 24 for closing or opening the side port 20 so fluid based material can continually flow into or out of the body. Essentially, any device that serves to control or limit the flow as desired can also perform the same function as the stopcock.

In the operation of the preferred embodiment, the needle 12 is inserted into a vein or artery of a patient to access blood. The blood flows through the needle 12 into the flashback chamber 20. The chamber 20 has a first transparent portion 32 through which a clinician can see if blood is filling the flashback chamber 20, thus indicating proper insertion of the needle 12 into the patient. The catheter 14 which is attached to the catheter hub 28 and side port hub 30 is then advanced as a unit over the needle 12 into the vein or artery.

The needle 12 is then withdrawn from the body and from the apparatus by the separation of the flashback chamber 20 from the side port hub 30 and catheter hub 28. By virtue of the self-sealing diaphragm 26, when the needle 12 is withdrawn, no blood escapes from the side port hub 30. Once the needle 12 is withdrawn, blood flows into the side port 38 by way of the catheter 14, catheter hub 28 and side port hub 30. To ensure that the blood is flowing properly, the second transparent portion 36 allows a clinician to view the interior 38 of the side port 24 to observe the blood flow, and view the side port hub interior 42 through third transparent portion 30 to observe blood flow therethrough. The stopcock 44 is in the open position to allow blood to flow through the side port 24 to be collected at a hook-up site 46 at the end of the side port 24. If, for instance, glucose or other fluid based drugs are desired to be introduced into the patient, the stopcock 44 is first repositioned to a closed position, preventing any flow through the side port 38. The instrument that collects the blood at the hook-up site 46 is withdrawn and replaced with an IV connected to the drug. The stopcock 44 is then repositioned in the open position to allow flow of the drug through the side port 24 in a direction into the patient. The fluid based material can then be introduced into the patient by way of the side port 38, side port hub 30, catheter hub 28 and catheter 14.

Figure 4A:
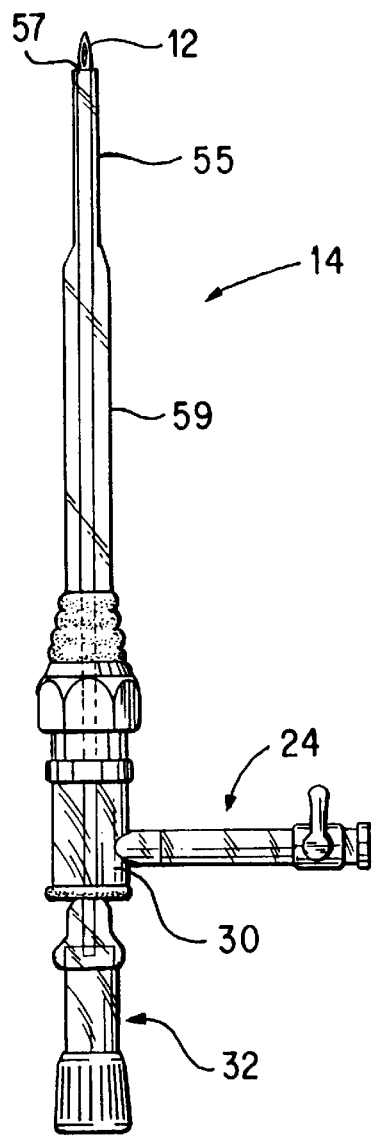
FIGS. 4a–4c are schematic representations of another embodiment of the present invention.

In another alternative embodiment, as shown in FIG. 4, the needle 12 is not separated from the central portion 16 after the catheter 14 is properly positioned in the interior of the body. The catheter 14 has a first portion 55 with a first diameter and a second portion 59 with a second diameter greater than the first diameter such that when the needle 12 is retracted from the first portion 55, fluid flows through the catheter 14 about the needle 12.

Figure 4B:
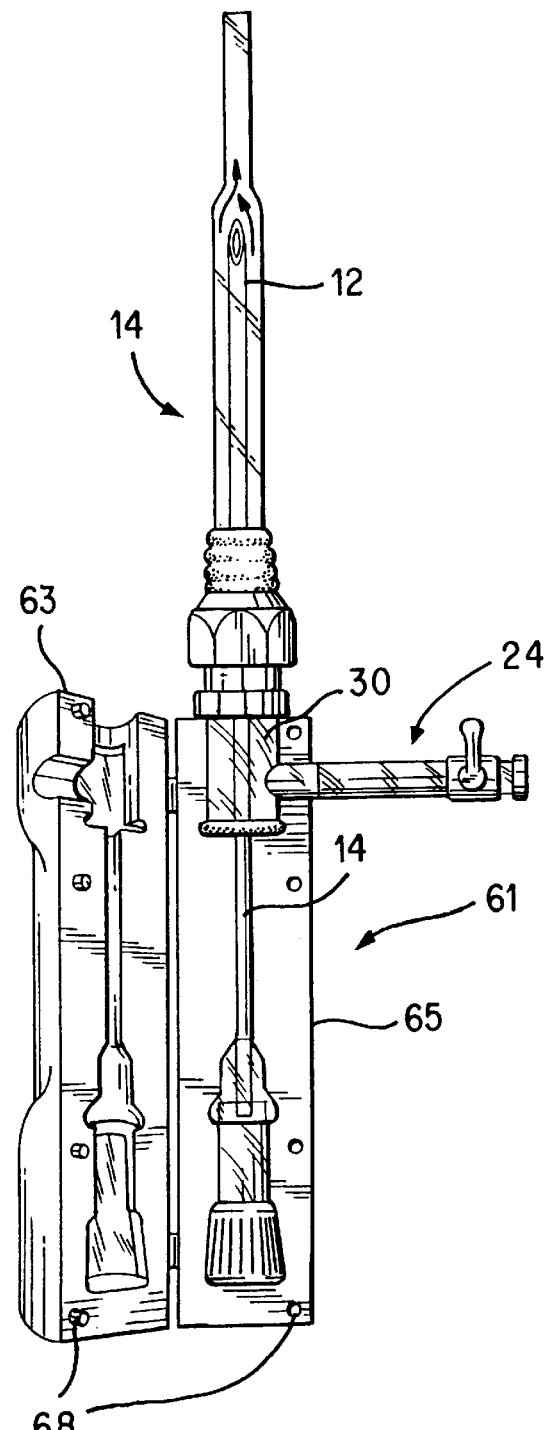
Figure 4C:
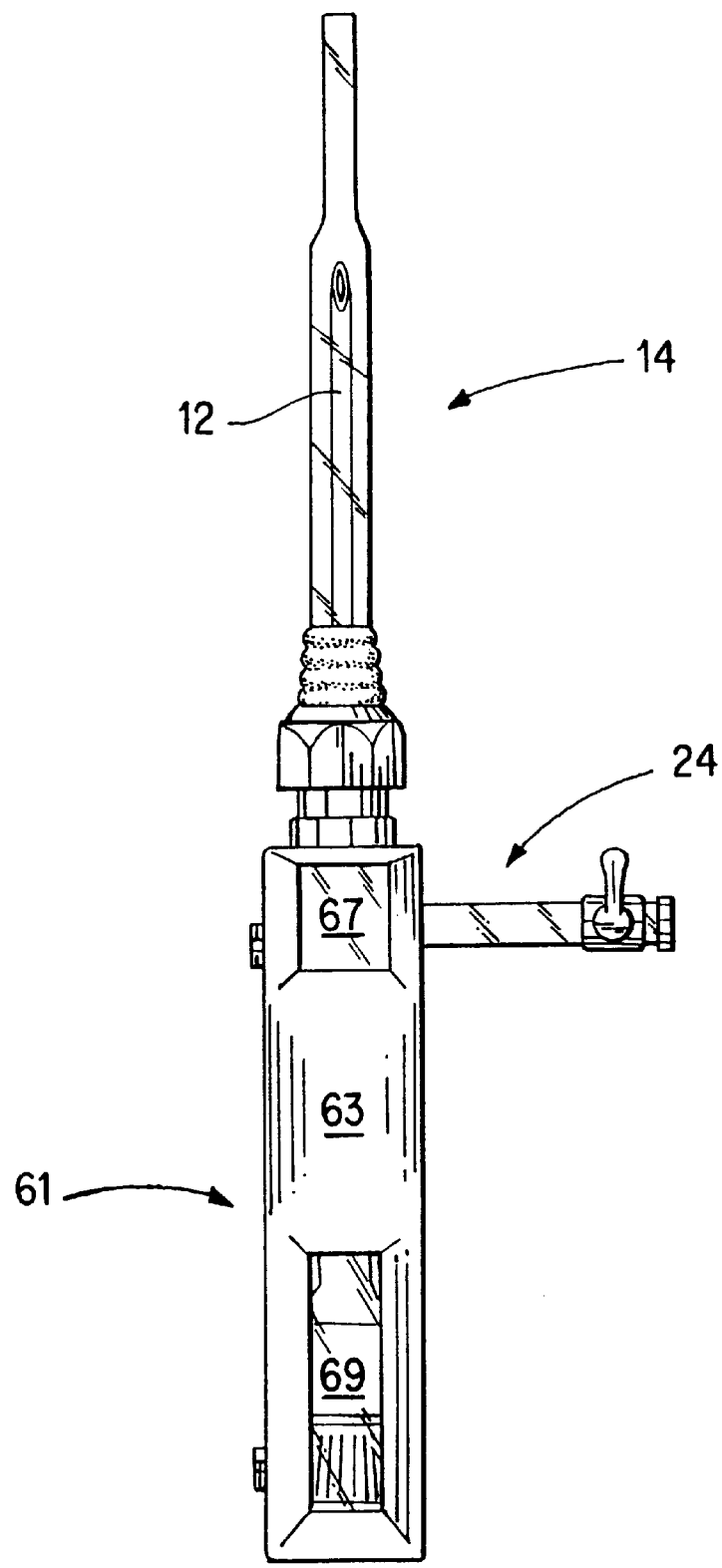

Once the needle 12 has been retracted, as shown in FIG. 4b, a housing 61 is used to encase the flashback chamber 20 and the portion of the needle 12 extending from the second end 26 so it is prevented from being disturbed. The housing 61 preferably also encases the side port hub 30 but allows the catheter hub 28 and the side port hub 30 to extend from it. Preferably, the housing 61 has a first side 63 and a second side 65 which are hingedly connected together. During use, the first side 63 and second side 65 are in an open position. When the needle is retracted, the first side 63 and second side 65 are closed together, as shown in FIG. 4c, and held in place by male/female lug connectors 68. The first side 63 can have a first transparent portion 67 and a second transparent portion 69 to view the side port hub 30 and the flashback chamber 32, respectively, therethrough. The housing 61 can be of molded plastic which has a depression shaped to receive the flashback chamber 20.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for the introduction or removal of liquid based material to or from a blood vessel of a patient by a clinician comprising:

means for connecting into the blood vessel to continuously introduce liquid based material into or remove liquid based material from the blood vessel, said connecting means fluidically sealed and self-sealing such that the liquid based material is prevented from escaping from the apparatus and coming into contact with the clinician at all times during installation and operation of the apparatus, the connecting means includes a guide mechanism which is adapted for connection into the blood vessel, the guide mechanism including a needle, the connecting means includes a catheter for transporting liquid based material, said catheter disposed about the guide mechanism, the connecting means includes a hollow central portion having a first end to which the catheter is sealingly fixed such that movement of the central portion and the catheter occurs in unison, and a flashback chamber fluidically connected to the central portion at a second end thereof, said needle extending through the central portion and into the flashback chamber by way of the first and second end of the central portion such that liquid based material flowing into the needle from the blood vessel fills the flashback chamber, said needle sealingly fixed to the flashback chamber and sealingly but slidingly connected to the central portion such that separation of the flashback chamber from the central portion and said catheter occurs without the escape of liquid based material from the central portion or the flashback chamber, said controlling means in fluidic connection with said central portion; and means for controlling whether liquid based material is continuously introduced into or removed from the blood vessel while the connecting means is in contact with the blood vessel without escape of the liquid based material therefrom, said controlling means in fluidic connection with said connecting means.

2. An apparatus as described in claim 1 wherein said central portion includes N side ports, where N≧1, in fluidic connection with said controlling means through which fluidic connection to desired objects can be made.

3. An apparatus as described in claim 2 wherein said controlling means includes a valve in fluid connection with each side port for closing or opening the side port so fluid based material can continually flow into or out of the body.

4. An apparatus as described in claim 3 wherein N can only be equal to 1.

5. An apparatus as described in claim 4 wherein the central portion at its second end has a self-sealing diaphragm through which said needle sealingly but slidingly extends.

6. An apparatus as described in claim 5 wherein the central portion includes a catheter hub having the first end, and a side port hub having the second end and from which the side port extends, said side port hub sealingly and fixedly attached to said catheter hub.

7. An apparatus as described in claim 6 wherein the flashback chamber has a first transparent portion through which the chamber interior can be viewed by the clinician.

8. An apparatus as described in claim 7 wherein the side port has a second transparent portion through which the side port interior can be viewed by the clinician.

9. An apparatus as described in claim 8 wherein the side port hub has a third transparent portion through which the side port hub's interior can be viewed by the clinician.

10. An apparatus as described in claim 9 wherein the valve is a two-way stopcock.

11. An apparatus as described in claim 1 wherein the catheter has a first portion with a first diameter extending from its first end and a second portion with a second diameter greater than the first diameter such that when the needle is retracted from the first portion, fluid flows through the catheter about the needle.

12. An apparatus as described in claim 11 wherein the second portion of the catheter is sealingly fixed to the first end of the hollow central portion of the connecting means.

13. An apparatus as described in claim 12 wherein said central portion includes N side ports, where N≧1, in fluidic connection with said controlling means through which fluidic connection to desired objects can be made.

14. An apparatus as described in claim 13 wherein said controlling means includes a valve in fluid connection with each side port for closing or opening the side port so fluid based material can continually flow into or out of the body.

15. An apparatus as described in claim 14 wherein N=1.

16. An apparatus as described in claim 15 wherein the central portion includes a catheter hub having the first end, and a side port hub having the second end and from which the side port extends, said side port hub sealingly and fixedly attached to said catheter hub.

17. An apparatus as described in claim 16 which includes a housing that encases the flashback chamber and the side port hub but out of which the catheter hub and side port hub extends.

18. An apparatus as described in claim 17 wherein the housing has a first side and a second side and encases the flashback chamber when the needle is in a retracted position such that fluid flows through the catheter about the needle, or when the needle is in an extended position such that the needle extends from the first end of the catheter.

19. An apparatus as described in claim 18 wherein the first side and second side are hingedly connected together.

20. An apparatus for the introduction or removal of fluid based material to or from a body of a patient by a clinician comprising:

means for communicating with the patient's body to continuously introduce fluid based material into or remove fluid based material from the patient's body, said communicating means fluidically sealed and self-sealing such that the fluid based material is prevented from escaping from the apparatus and coming into contact with the clinician at all times during installation and operation of the apparatus, said communicating means including a catheter disposed about a needle, said catheter has a first portion with a first diameter extending from its first end and a second portion with a second diameter greater than the first diameter such that when the needle is retracted from the first portion, fluid flows through the catheter about the needle; and means for controlling whether fluid based material is continuously introduced into or removed from the body's interior while the communicating means is in contact with the body without the escape of the fluid based material therefrom, said controlling means in fluidic connection with said communicating means.

21. An apparatus as described in claim 20 wherein the communicating means includes a hollow central portion having a first end to which the second portion of the catheter is sealingly fixed such that movement of the central portion and the catheter occurs in unison, and a flashback chamber fluidically connected to the central portion at a second end thereof, said needle extending through the central portion and into the flashback chamber by way of the first and second end of the central portion such that fluid based material flowing into the needle from the body fills the flashback chamber, said needle sealingly fixed to the flashback chamber and sealingly but slidingly connected to the central portion, said controlling means in fluidic connection with said central portion.

22. An apparatus as described in claim 21 wherein said central portion includes N side ports, where N≧1, in fluidic connection with said controlling means through which fluidic connection to desired objects can be made.

23. An apparatus as described in claim 22 wherein said controlling means includes a valve in fluid connection with each side port for closing or opening the side port so fluid based material can continually flow into or out of the body.

24. An apparatus as described in claim 23 wherein N=1.

25. An apparatus as described in claim 24 wherein the central portion includes a catheter hub having the first end, and a side port hub having the second end and from which the side port extends, said side port hub sealingly and fixedly attached to said catheter hub.

26. An apparatus as described in claim 25 which includes a housing that encases the flashback chamber and the side port hub but out of which the catheter hub and side port hub extends.

27. An apparatus as described in claim 26 wherein the housing has a first side and a second side and encases the flashback chamber when the needle is in a retracted position such that fluid flows through the catheter about the needle, or when the needle is in an extended position such that the needle extends from the first end of the catheter.

28. An apparatus as described in claim 27 wherein the first side and second side are hingedly connected together.

29. An apparatus for the introduction and removal of liquid based material to or from a vein or artery of a patient by a clinician comprising:

a guide mechanism which is adapted for connection into the vein or artery;

a catheter for transporting liquid based material, said catheter disposed about the guide mechanism;

a hollow central portion having a first end to which the catheter is sealingly fixed such that movement of the central portion and the catheter occurs in unison, and a second end and through which the guide mechanism slidingly extends;

a self-sealing diaphragm fixedly attached to the second end and exposed such that the guide mechanism extends through the diaphragm without passing through any other structure such that liquid based material is prevented from escaping from the apparatus and coming into contact with the clinician at all times during installation and operation of the apparatus wherein said guide mechanism is a needle;

N side ports extending from said central portion through which liquid based material can flow therefrom, where $N \geqq 1$, each side port having a valve in fluidic connection with it for closing or opening the respective side port so liquid based material can continually flow into or out of the blood vessel; and a flashback chamber fluidically connected to the central portion at the second end thereof, said needle extending through the central portion and into the flashback chamber by way of the first and second end of the central portion such that liquid based material flowing into the needle from the vein or artery fills the flashback chamber, said needle sealingly fixed to the flashback chamber and sealingly but slidingly connected to the central portion through the diaphragm such that separation of the flashback chamber from the central portion and said catheter occurs without the escape of liquid based material from the central portion or the flashback chamber.

* * * * *